Feb. 11, 1975 M. K. PARKER Plant Pat. 3,687
PECAN TREE
Filed Jan. 14, 1974
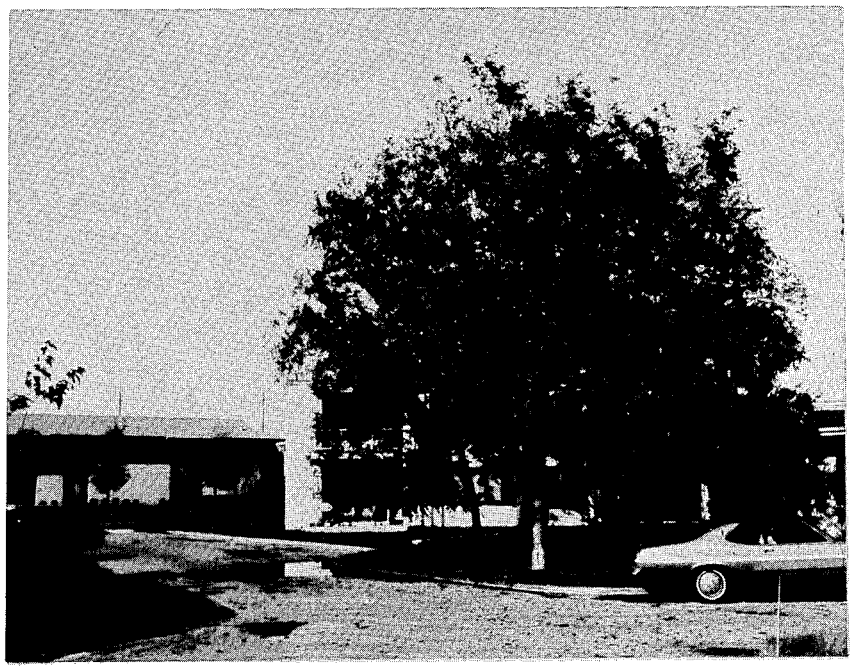
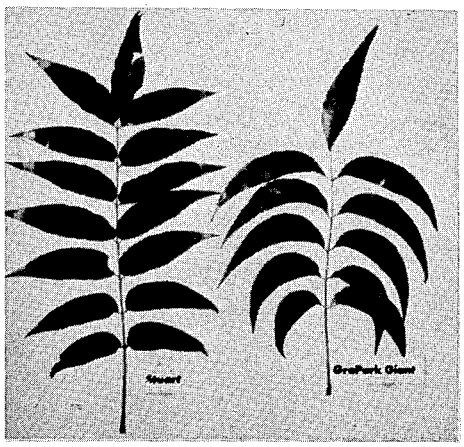
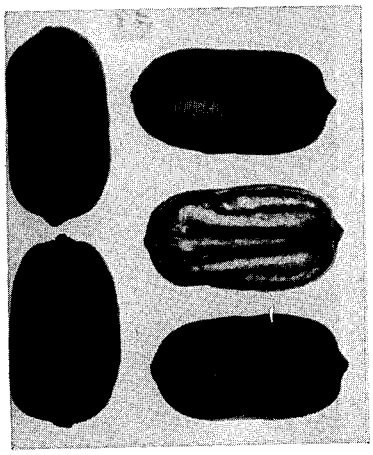

United States Patent

Plant Pat. 3,687

Patented Feb. 11, 1975

3,687

PECAN TREE

Micral K. Parker, Grand Prairie, Tex., assignor to O. S. Gray, Arlington, Va.

Filed Jan. 14, 1974, Ser. No. 433,120

Int. Cl. A01h *5/03*

U.S. Cl. Plt.—31 1 Claim

ABSTRACT OF THE DISCLOSURE

A new variety of pecan tree distinguished by a vigorous and sturdy growth habit and its abundant production of very large thin shelled nuts having unusually plump, smooth and clean kernels the halves of which readily separate from the shell, cork and septum when the shell is cracked to produce a high yield of marketable meats.

BACKGROUND OF THE INVENTION

My new variety of pecan tree originated as a seedling of unknown parentage selected from a group of seedlings resulting from my planting in 1947 of a number of selected seeds on the grounds of my residence at Grand Prairie, Tex. Careful culture and observation led to my discovery that one was particularly distinguished because of its precosity and its prolific production of unusually large nuts from which very attractive kernels could be easily separated from the shell.

Asexual propagation of this new pecan tree by both budding and grafting was begun at nursery grounds at Arlington, Tex., this propagation being carried on at my direction by O.S. Gray, and our careful observation during the past four years of the pecan trees so produced has shown that from generation to generation, the favorable characteristics of the original tree hold true and appear to be firmly fixed in all respects.

DESCRIPTION OF THE DRAWINGS

My new variety of pecan tree is illustrated by the accompanying photographic drawings in which:

FIG. 1 is a view showing the original discovery tree;

FIG. 2 is a view showing nuts of the new variety of pecan tree, one having its shell partly removed to show the kernel; and FIG. 3 is a view showing a leaf of the new tree compared with a leaf of the commonly grown Stuart variety of pecan tree.

DESCRIPTION OF THE NEW TREE

Growth habit

Vigorous and spreading with numerous bearing branches and twigs throughout the foliage mass and a prolific formation of fruiting clusters. The original tree of this new variety, shown in FIG. 1, has now grown to a height of about 30 to 35 feet with a spread about equal to its height. The tree is also precocious with a very prolific production of unusually large nuts at an earlier than the usual age.

Foliage

The leaves are of normal abundance and are of odd-pinnate compound form, usually with 11 to 13 leaflets which under normal conditions measure about 1¾ inches wide and 6 inches long. The leaflets are often of a curved form, and are somewhat lanceolate, tapering to an acuminate tip and are not as dark green in color as those of the widely grown Stuart variety. As shown at the right in FIG. 3, the leaflets of my new variety are narrower and more pointed than those of Stuart which appear at the left in FIG. 3.

Buds

The buds of this new variety of pecan tree are closely spaced on the branches resulting in more numerous fruiting branches and a greater than usual production of nut clusters. In shape, the bud is generally ovate.

Flowers

The flowers of this tree appear early in spring and, as is usual with pecans, both pistillate and staminate flowers are produced on the same tree. Flowers begin to form early in the life of the tree and this precocious habit is one of its distinguishing characteristics.

Nuts

Ripening habit: The nuts ripen evenly and somewhat earlier than mid-season, separating easily and cleanly from the shucks at harvest time.

Size and shape: The nuts of my new variety of pecan tree are of unsually large size, selected specimens measuring a full 2 inches in length and 1⅛ inch in diameter, and under good growing conditions, the count will be about 32 nuts per pound. The nut outline is somewhat blocky or rectangular as viewed from either end, as well as from the side, with a somewhat bluntly pointed apex. The body of the nut is slightly flattened from dorsal to ventral sides, as well as laterally, and being rather blunt at each end, the nut has a box-like shape that is the particularly distinguishing characteristic of the nuts produced by my new pecan tree.

Quantity: The prolific production of nut clusters, each with 3 to 6 nuts, results in an unusually heavy yield.

Shell color: The shell color of the new nut is a light brown with a scattering of dark brown pin-point size dots, mostly concentrated toward the basal end, and with dark brown, irregularly shaped stripes extending lengthwise along the apical half of the nut body.

Shell and husk: The shell of this nut is extremely thin, averaging half the thickness of the well known Stuart variety (unpatented). The unsual thinness of the shell is a distinguishing characteristic of this new variety. The husk is of average thickness.

Cracking quality: The very thin shell of this new nut and a small amount of space between the shell and the kernel permit easy cracking by hand or by machine without crushing the kernel, resulting in an exceptionally high percentage of whole half-kernels.

Kernels: The kernels are of light brown color and of excellent flavor, with a very light, almost indistinguishable veining over the surface. The wide primary and less prominent secondary grooves extending lengthwise along the dorsal sides of the kernels release the "cork" readily when the nuts are cracked and the kernel halves are released easily from the septum that divides them. The smooth plump appearance of the kernel, the absence of prominent wrinkles and indentations, is particularly noticeable especially in a pecan nut of this size.

Shelling quality: The unusually thin shell of this new nut results in a very high kernel weight compared to the total weight of the nut. The cracking tests average 58 pounds of kernels resulting from each 100 pounds of whole nuts and selected nuts have yielded as high as 62% kernel weight.

Disease resistance

This pecan tree and those test trees propagated from it have shown no sign of scab disease.

This new variety of pecan tree is particularly distinguished by its precocious bearing habit as shown by its abundant production of nuts on young trees during their third and fourth growing seasons, and by its prolific production of large size nuts with extremely thin shells. The nuts of this new tree are characteristically blocky in shape with excellent cracking qualities and with smooth, delightfully flavored, attractive light golden brown kernels.

The nuts of this new variety of pecan tree are particularly distinguished from other varieties by being somewhat flattened on four sides and by their rather blunt ends. The nut of the Stuart variety is almost round at the basal end and is somewhat flattened only from two sides at the apical end. The new nut is also easily distinguished by its shape from other varieties such as the GraBohls variety (P.P. 3,434) which characteristically tapers to both the basal and apical ends and has a rounded rather than flattened body.

The shell color of this new variety is brighter than the almost grayish cast of the widely grown Stuart variety but is of a somewhat darker brown color than the bright tan of the GraBohls variety.

The foliage of this new pecan tree is not as dark green in color as that of the Stuart variety and the leaflets are somewhat narrower and more pointed toward the apex than those of Stuart, often being recurved.

The claim:

1. A new variety of pecan tree, substantially as herein shown and described, characterized by its prolific production of large sized and very thin shelled nuts which are distinguished by their box-like and blunt-ended body form, and by the very large weight percentage of the kernels which are characteristically smoother and freer from wrinkles than those of most other nut varieties.

No references cited.

ROBERT E. BAGWILL, Primary Examiner